(12) United States Patent
Rousseau et al.

(10) Patent No.: US 9,770,241 B2
(45) Date of Patent: Sep. 26, 2017

(54) SUTURE WITH TRIM FORMED TIP

(71) Applicant: Ethicon, Inc., Somerville, NJ (US)

(72) Inventors: Robert Anthony Rousseau, Ottsville, PA (US); David C. Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 248 days.

(21) Appl. No.: 14/295,673

(22) Filed: Jun. 4, 2014

(65) Prior Publication Data
US 2015/0351752 A1   Dec. 10, 2015

(51) Int. Cl.
*B29C 51/32* (2006.01)
*A61B 17/06* (2006.01)
*A61L 31/14* (2006.01)
*A61B 17/00* (2006.01)

(52) U.S. Cl.
CPC ........ *A61B 17/06195* (2013.01); *A61B 17/06* (2013.01); *A61B 17/06004* (2013.01); *A61B 17/06066* (2013.01); *A61B 17/06166* (2013.01); *A61L 31/148* (2013.01); *A61B 2017/00526* (2013.01); *A61B 2017/06185* (2013.01); *Y10T 29/49803* (2015.01)

(58) Field of Classification Search
CPC .............. A61B 17/06; A61B 17/06195; A61B 17/06166; A61B 17/06066; A61B 17/06004; A61B 2017/00526; A61L 31/148; Y10T 29/49803
See application file for complete search history.

(56) References Cited

U.S. PATENT DOCUMENTS

| | | |
|---|---|---|
| 2,067,568 A | 1/1937 | Moritz |
| 2,958,929 A | 11/1960 | Vineberg et al. |
| 3,890,975 A | 6/1975 | McGregor |
| 3,926,194 A | 12/1975 | Greenberg et al. |
| 4,027,519 A | 6/1977 | Bachle |
| 4,832,025 A | 5/1989 | Coates |
| 5,007,922 A | 4/1991 | Chen et al. |

(Continued)

FOREIGN PATENT DOCUMENTS

| | | |
|---|---|---|
| AU | 511397 | 10/1977 |
| EP | 443704 | 8/1991 |

(Continued)

*Primary Examiner* — Galen Hauth
(74) *Attorney, Agent, or Firm* — E. Richard Skula

(57) ABSTRACT

The present invention discloses methods for producing a surgical suture having a reduced cross-sectional area portion from monofilaments fibers of various polymeric and metallic materials. Also disclosed are novel sutures having novel tips. Novel suture tipping apparatuses are also disclosed. The monofilament is subjected to the application of thermal treatment coupled with application of mechanical shaping of the fiber element to produce a deformed cross sectional portion of the suture body. The deformed suture body region is subsequently subjected to a trimming operation within a punching/stamping die. The reduced section of the suture body region and is severed to form a suture having a reduced-cross sectional area end portion. Preferably, each reduced region is severed approximately in the center of the trimmed reduced cross sectional area portion to form a suture having both ends of a reduced cross-sectional area.

15 Claims, 15 Drawing Sheets

(56) References Cited

U.S. PATENT DOCUMENTS

| | | | |
|---|---|---|---|
| 5,131,131 A | 7/1992 | Proto | |
| 5,707,391 A | 1/1998 | Carpentieri | |
| 8,216,497 B2 | 7/2012 | Lindh, Sr. et al. | |
| 2001/0008979 A1 | 7/2001 | Bonutti | |
| 2002/0077631 A1* | 6/2002 | Lubbers | A61B 17/0401 606/232 |
| 2010/0084780 A1* | 4/2010 | Lindh, Sr. | A61B 17/06166 264/145 |
| 2010/0139883 A1 | 6/2010 | Stametz et al. | |

FOREIGN PATENT DOCUMENTS

| | | |
|---|---|---|
| FR | 2687565 | 8/1993 |
| GB | 1218057 | 1/1971 |

* cited by examiner

SUTURE WITH TRIM FORMED TIP

FIELD OF THE INVENTION

The field of art to which this invention relates is surgical sutures, in particular, methods of tipping surgical sutures, surgical sutures made by such methods, and apparatuses for tipping surgical sutures.

BACKGROUND OF THE INVENTION

Surgical sutures and attached surgical sutures are well known in the art. During the course of a surgical procedure, it is typically necessary for the surgeon to use surgical needles and attached sutures for a variety of purposes, including to approximate tissue. It is desirable, in many of these procedures, that the maximum diameter of the needle, typically the diameter at the blunt or proximal end of the needle, and the maximum diameter of the suture be as close to the same size as possible, and it is also advantageous for the suture diameter to be larger. This design is necessary or desirable so that a hole and pathway in tissue resulting from a surgeon passing the needle through the tissue during a surgical procedure is substantially filled by the body of the suture. This is especially important when joining or approximating highly vascularized tissue in order to prevent oozing or seepage of blood through the pathway and hole produced by the needle. In addition, pathways for bacteria are effectively closed off to prevent infections. Originally, most surgical needles had an eye at their blunt or proximal ends through or in which a surgical suture was mounted or attached. As can be appreciated, this meant that the blunt end of the needle had to have a sufficient size to allow for an eye to be placed in the blunt end of the needle and to accommodate at least double the maximum diameter of a suture strand folded around the eye feature of the needle. This doubling of the suture and the requisite increased size of the blunt end of the needle resulted in a needle-suture combination with a large cross-sectional area that was passed through the tissue. The resulting hole and pathway in the tissue, produced when the needle was passed through tissue, was substantially greater than the cross-sectional area of the attached suture remaining within the tract to approximate or fix the tissue; as described herein, such a pathway may lead to post-implantation complications such as bleeding, infections, etc.

Over the years, in order to improve surgical procedures and patient outcomes, various techniques have been developed to eliminate the eye in the blunt or proximal end of the needle and find other techniques or methods by which a suture strand can be attached to the blunt or proximal end of a surgical needle. One example of an improved suture attachment technique that has been developed is the forming of a channel in the blunt or proximal end of a needle by a conventional metal forming process. In order to attach an end of a suture to a surgical needle having a channel, the distal end of the suture is placed in the channel and the channel is mechanically swaged in a conventional manner to mechanically secure the suture end in the needle channel. Another technique known in this art for attaching suture strands to surgical needles is to drill a bore hole into the proximal end of a surgical needle using conventional processes such as laser drilling and mechanical drilling. In a similar manner, the distal end of a surgical suture is placed into the bore hole and the proximal end of the needle containing the bore hole is conventionally mechanically swaged, although other attachment or securement methods may be used such as gluing. As can be appreciated, it is still required that the diameter or maximum dimension of the blunt or proximal end of a needle having a suture mounting channel or bore hole be substantially larger than the diameter of the body of an attached suture, and hence when such needle-suture combinations are used to join tissue, the suture still does not completely fill the resulting hole and pathway in tissue formed by the needle.

Processes have evolved that may produce a multi-diameter suture, wherein the body of the suture is substantially larger than the portion of the suture (i.e., the tip) that is attached or mounted to a non-eyed needle, either in a channel or bore hole. The processes known in the art for producing reduced diameter suture tips typically alter the flexibility of the suture in the reduced sections in a negative manner by causing an increase in fiber stiffness or a loss of suture diameter consistency, thereby producing variable needle attachment strength. There remains a need in this art for novel processes and apparatuses to produce a suture with a novel tip section having a reduced cross sectional area that maintains the suture material properties of yield stress and suture flexibility at the needle attachment location, while providing consistent needle attachment strength through improved suture tip physical dimensions. There have been various approaches to suture tipping in the art.

U.S. Pat. No. 3,890,975 (McGregor), discloses a braided suture that is subjected to sizing through the application of tension when dipped in a liquid resin solution. The suture is dried to remove the solvent and to allow the coated region to solidify. Since the braided suture is subjected to tension, there is a reduction in diameter as the braided elements begin to align axially thereby compacting the core fibers. As the liquid resin dries, the coated region or tip of suture containing the tensioned coated fibers is locked into the reduced diameter configuration. The uncoated region resumes the original diameter when the tension is released. The sizing operation is conducted to ensure that the suture will release at a more consistent force from the needle after crimping. This process is only applicable to braided sutures, and the final suture diameter is dependent upon the quality or density of the braided suture utilized.

U.S. Pat. No. 4,832,025 (Coates), discloses a method for treating braided sutures that involves melt fusion of the tip region for insertion into a surgical needle. The suture is heated to an elevated temperature sufficient to effectively "melt fuse" a portion of the outer filaments of the multifilament suture. Such temperatures are typically in the range of about 260° C. to 300° C. (500° F. to 572° F.). The suture then stiffens upon cooling. Surface melting of the outer filaments has the effect of holding the filaments together when the suture is cut. It also causes stiffening of the suture which facilitates insertion of the suture end into the drilled bore hole of a needle. However, this melt fusion process has several significant drawbacks. Firstly, the melt fusion of filaments weakens the suture, whose tensile strength is degraded in proportion to the extent of melt fusion. Secondly, melt fusion causes an irreversible change in the suture filaments, which results in permanent stiffening and significant loss of the outer braided sheath tensile strength; and, this may result in sheaths that fracture and release independent of the core fibers causing bunching of the suture sheath during use.

U.S. Pat. No. 5,007,922 (Chen, et al.) discloses a method of producing monofilament sutures with regions of reduced diameter suture. The suture is wound in a helical or spiral configuration about a drum unit. The drum unit contains a region that is capable of expanding to produce an effectively larger perimeter dimension about the drum through the use of a split drum design. Once the fiber is wound about the perimeter of the drum, a heating element is positioned against the side of the drum tangentially along an axis that is parallel to the central axis of the drum. The heating element increases the temperature of any suture that is exposed along this line of contact along the side of the drum. After a satisfactory amount of heating has occurred, the drum is actuated such that the perimeter of the drum is increased. Since the suture is wound about the perimeter of the drum, the regions of heated suture are drawn down to accommodate the change in this dimension. This process results in reduced diameter regions within the suture that are highly oriented, beyond the orientation of the remaining non-heated regions of the suture. In addition to the change in molecular alignment, the resultant suture diameters of the exposed regions will vary depending upon the amount of deformation experienced in either overheated or underheated segments of fiber windings.

U.S. Pat. No. 8,216,497 (Lindh, et al.) discloses various methods for forming tissue holding devices having predetermined shapes suitable for use in surgical applications, and devices formed in accordance with such methods are also provided. These methods include press-forming methods, and press-forming methods in combination with profile punching. Tissue holding devices formed in accordance with such methods include various configurations for a core and a plurality of tissue holding elements, such as barbs, extending outwardly from the core. The processes provide a method to shape an extruded fiber, at an elevated temperature, into a broader configuration that enables punch press-type technology to be applied to remove sections of the formed fiber component to form solid barbed elements. Their intention is to maintain a center region that is closer to the cross-sectional area of a traditional suture with appendages essentially extending from this core. Since the cross-sectional area of the core of the fiber is sized to be equivalent to a comparative non-barbed suture, the strength is essentially the same as the traditional comparative fiber. The process, as disclosed, relies on the displacement of the entire length of fiber to produce a uniform billet that is to be subjected to punching of the fiber. The punching operation produces a fiber with an oval configuration with extensions from a central core region to ensure that the fiber meets the knot tensile strength requirements for a comparably sized round suture. Due to the large displacement of the entire fiber volume to create a pre-punch billet, the straight tensile strength of the suture body is reduced relative to an unformed extruded suture because of the loss of orientation in the bulk forming process. Additionally, due to the reliance of bulk billet production, the process of forming and cutting cannot be linked into a continuous form and cut process due to the space required for said production.

Although the suture tipping processes of the prior art are adequate for their intended purpose, there are certain deficiencies attendant with their use. The deficiencies include loss of flexibility of the suture in the tipped region, fibrillation of the tipped region, alteration of the suture material yield stress, variability in finished tip geometry and limited applicability to non-braided sutures.

There is a need in this art for novel suture tipping processes and novel apparatuses for producing monofilament sutures having novel tip structures or sections that overcome the disadvantages of the processes of the prior art.

SUMMARY OF THE INVENTION

It is an object of the present invention to provide a needle-suture combination, which when used to join tissue, results in the hole pathway in tissue produced by the needle being substantially filled by the monofilament suture joining the tissue.

It is a further object of the present invention to provide a novel process for producing novel suture tip section on a monofilament suture.

It is yet a further object of the present invention to provide a suture having a tip with a novel cross-section.

Still yet a further object of the present invention is to provide a novel apparatus for producing a novel tip section on a monofilament suture.

Accordingly, the present invention discloses methods for producing a surgical suture having a reduced cross sectional area portion from monofilaments of various polymeric materials. The monofilament is subjected to the application of mechanical shaping of the fiber element, optionally coupled with thermal treatment, to produce a deformed cross-sectional portion of the suture body. The deformed suture body region is subsequently subjected to a trimming operation within a punching or stamping die. The reduced section of the suture body region is severed to form a suture having a reduced cross-sectional area end portion. Preferably, each reduced region is severed approximately in the center of the trimmed reduced cross-sectional area portion to form a suture having both ends with a reduced cross-sectional area, although it may be severed in other locations.

An aspect of the present invention is a method of tipping a monofilament surgical suture, consisting of the following steps. A length of monofilament surgical suture is provided having a first end, a second end, and a body having a maximum cross-sectional dimension. The suture is formed to have a formed section having a transition section and a tip section. At least part of the formed section is trimmed to create a trimmed section to provide a suture having a transition section and a tip section, the tip section having a cross-section with an outer perimeter. The maximum dimension of the cross-section of the tip section is less than the maximum cross-sectional dimension of the body of the suture.

Another aspect of the present invention is a monofilament suture having a formed distal tip. The suture has a suture filament having a body, a proximal end, and a distal end. The body of the suture has a maximum cross-sectional dimension. The filament has a tip section on the distal end, and, a transition section between the suture filament body and the tip section. The tip section has a cross-section having an outer perimeter and a maximum dimension. The perimeter has at least two connected segments. The maximum dimension of the cross-section of the tip section is less than the maximum cross-sectional dimension of the body of the suture.

Yet another aspect of the present invention is an apparatus for tipping a monofilament surgical suture. The apparatus has an alignment frame for receiving a monofilament suture strand, preferably having a first clamp and a second clamp. There is a forming press for forming a section of the suture. The press has a base plate, and a slidably mounted upper plate allowing for vertical motion. A lower forming die is mounted to the base plate. The lower forming die has a planar top surface, a forming cavity, and walls extending upwardly from the top surface to form part of the cavity; the walls have a top. An upper forming die is mounted to the upper plate. The upper forming die has a planar lower surface, a forming cavity, and walls extending downwardly from the lower surface to form at least part of the cavity; the walls have a top. Edges extend from the tops of the walls of the upper and lower forming dies. The apparatus has a cutting press. A punching die set is mounted to the cutting press for cutting a formed suture section into a trimmed suture tip. The punching die set has an upper die plate, a lower die plate, and at least one cutting die. The alignment frame is removably mounted to the forming press between the upper and lower forming dies, and the alignment frame is removably mounted to the cutting press between the upper and lower plates of the die set.

Still yet another aspect of the present invention is an apparatus for tipping a monofilament surgical suture. The apparatus has an alignment frame, preferably having a first clamp and a second clamp, for receiving a monofilament suture strand. There is a forming press for forming a section of the suture. The press has a base plate, and a slidably mounted upper plate allowing for vertical motion. A lower forming die is mounted to the base plate. The lower forming die has a planar top surface, a forming cavity, and walls extending upwardly from the top surface to form part of the cavity, the walls having a top. An upper forming die is mounted to the upper plate. The upper forming die has a planar lower surface, a forming cavity, and walls extending downwardly from the lower surface to form at least part of the cavity, the walls have a top. Cutting edges extend from the tops of the walls of the upper and lower forming dies.

These and other aspects and advantages of the present invention will become more apparent from the following description and accompanying drawings.

BRIEF DESCRIPTION OF THE DRAWINGS

FIG. 2A is a cross-sectional view of the tip section of the suture of FIG. 2 taken along view line 2A-2A illustrating the novel cross-section.

DETAILED DESCRIPTION OF THE INVENTION

Figure 1:
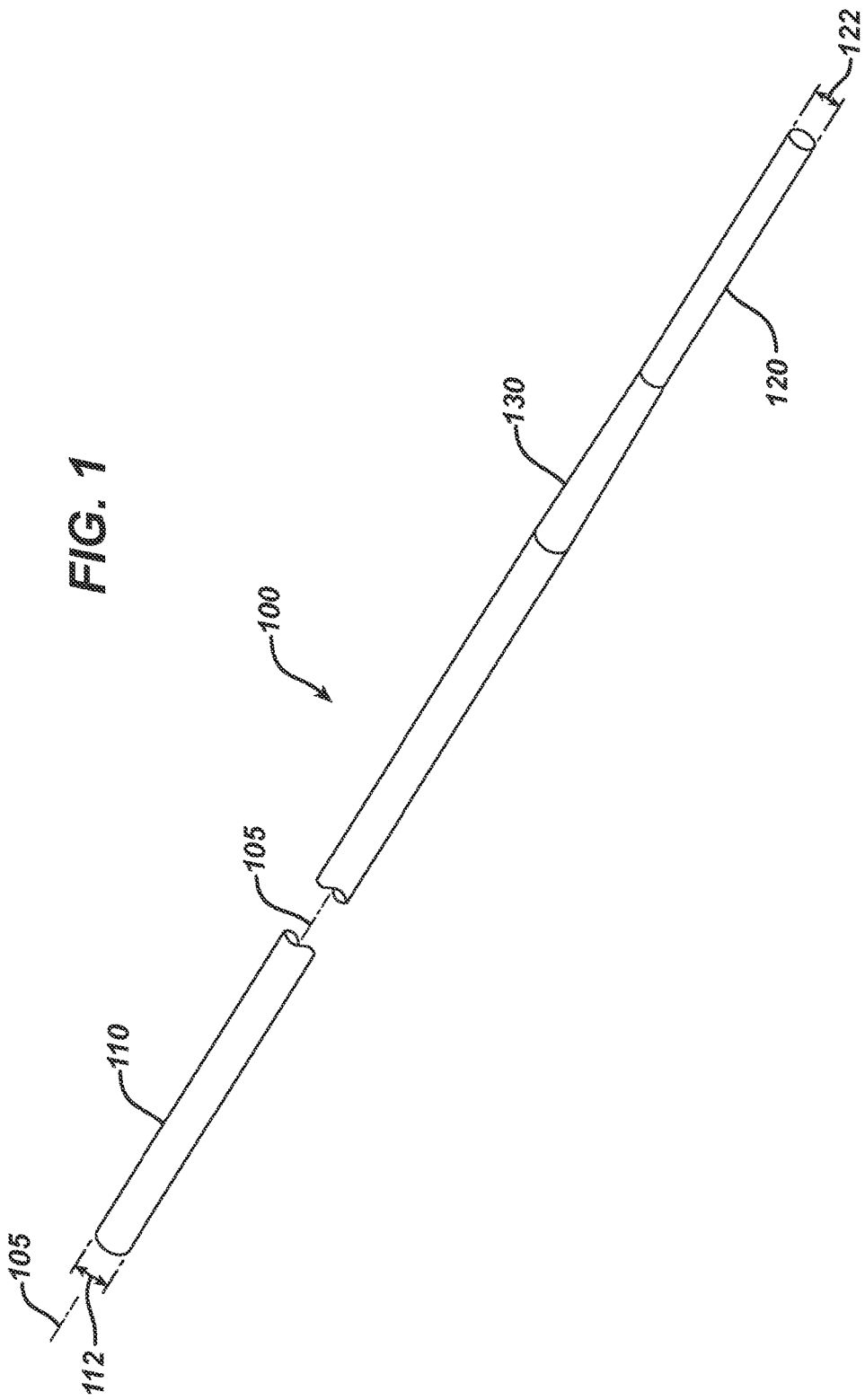
FIG. 1 is a perspective view of an end of monofilament suture device having a tip with a novel configuration that has been produced through the novel process of the present invention.

The novel tip forming process of the present invention is useful with any monofilament suture. Examples of commercially available monofilament sutures that can be tipped with the process of the present invention include PROLENE® suture, PRONOVA® suture, PDS® suture, NUROLON® suture, surgical gut suture, and stainless steel sutures and the like. The sutures may be made from conventional biocompatible polymeric materials, both synthetic and natural materials such as surgical gut. The sutures may be made from absorbable or non-absorbable polymers, or combinations thereof. The absorbable polymers include conventional biocompatible, polymers such as lactide, polylactic acid, polyglycolic acid, glycolide, polydioxanone, polycaprolactone, copolymers and blends thereof and the like. The nonabsorbable polymers include conventional biocompatible polymers such as, polyolefinspolyamides (polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride), polyolefins (e.g., polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene including ultra high molecular weight polyethylene and the like and combinations thereof. The sutures may also be made from conventional biocompatible metals and metal alloys including surgical stainless steels, Nitinol, etc.

The sutures that may be tipped using the novel process of the present invention may have a variety of conventional suture sizes ranging from size 5 to size 10-0 The sutures tipped by the novel processes of the present invention are mounted to conventional surgical needles made from conventional biocompatible materials such as metal alloys including surgical stainless steel, tungsten-rhenium alloys, etc. If desired, the surgical needles may be made from other biocompatible materials including ceramics, polymeric materials and composites, etc. The needles will preferably have proximal needle mounting ends having drilled bore holes or channeled features for receiving a distal suture tip and mounting it to the needle. The suture tips may be mounted or secured (i.e., attached) to the proximal suture mounting ends of the surgical needles by conventional attachment techniques including mechanical swaging, gluing, melting, etc. The maximum dimension at the proximal mounting end of the needle after the suture tip has been mounted and secured (i.e., attached) in place will preferably be less than or equal to the maximum diameter of the body of the needle.

Referring to FIG. 1, a monofilament suture device 100 is illustrated having a novel tip section 120 that has been produced through a novel process of the present invention is illustrated. The suture 100 is seen to have a filament or body section 110, distal tip section 120, and tapered transition section 130, which in this embodiment has a tapered configuration. The suture 100 has longitudinal axis 105. The suture filament section 110 is preferably extruded as a substantially cylindrical fiber having a main body diameter 112. The suture filament section 110 may be extruded to have additional geometries including cross-sections that are oval, elliptical, square, triangular, polygonal, combinations of curved sections and straight sections, etc. In order to attach the suture 100 to a surgical needle of a reduced outer diameter, it is necessary to provide an appropriate tip at the distal end of the suture 100. The suture 100 is seen to have a proximal tip 120, the end that will be mounted to the proximal end of a surgical needle. Tip 120 has been subjected to the novel process of the present invention in order to reduce the diameter of the main body of the suture and form the tip section 120. In addition to the reduced and formed proximal tip section 120, there is a transition region 130 (tapered as shown although not limited thereto) that serves to transition from the main body diameter 112 of the suture filament section 110 to the diameter 122 of proximal tip 120. The transition region 130 serves the purpose of minimizing localized stress effects on the fiber during tensioning. In preferred embodiment, the transition region 130 has a tapered configuration.

Figure 2:
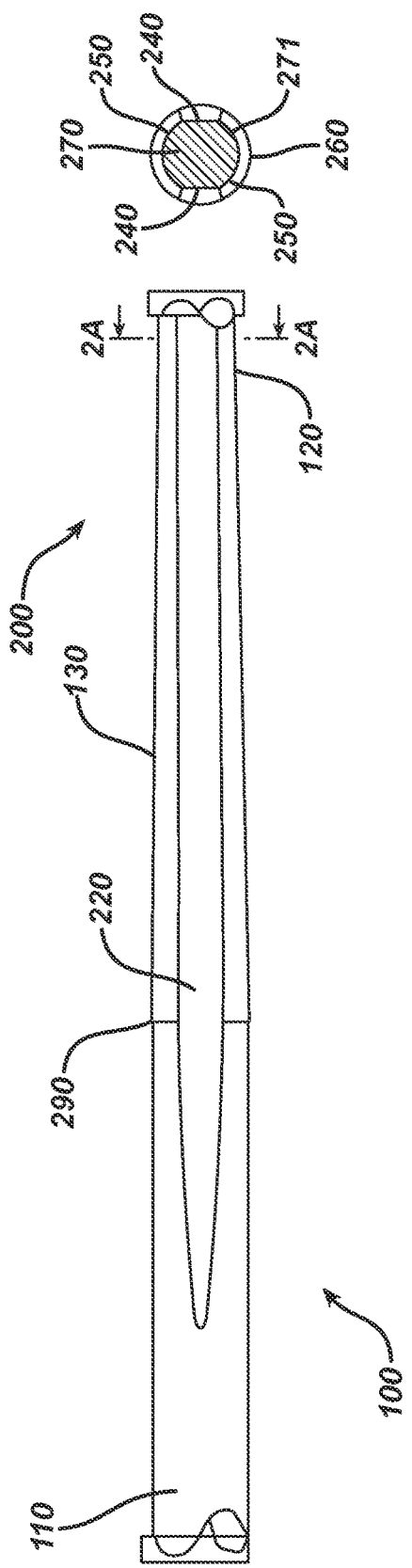
FIG. 2 is a side view of the suture of FIG. 1, after the tip section has been formed and trimmed in accordance with present invention.

The novel suture tip 120 of the present invention is further illustrated in FIG. 2. The proximal tip diameter 122 of tip section 120 has been modified through the forming and trimming process of the present invention. The modified tip section 120 has a non-round configuration 200 as seen in the cross-sectional view of FIG. 2A. The configuration is seen to have opposed arcuate sections 250 joined by flat or linear sections 240. The diameter 122 is the maximum dimension between the arcuate curved sections 250 passing through the center of the configuration 200. The transition region 130 of the suture body is illustrated as a tapered section that transitions the suture 100 from the main body diameter 112 of body section 110 to the diameter 122 of the non-round proximal tip region 120 having configuration 200. The distal end of suture 100 is seen to have opposed lateral trim regions 220 extending from a distal section of the fiber body 110 through the tapered transition section 130 and to tip section 120. The arced portions of the transition region 130 are formed initially through the application of sufficient pressure that causes excess material to flow laterally from the central region of the suture body 110 while the upper and lower portions of the suture 100 conform to the radial geometry within the upper and lower forming dies as described herein. Additionally, during the application of pressure during the initial forming step, heat, produced through simple resistance heaters, radio frequency generators, plasma, laser or ultrasonic equipment, may be utilized to assist in the mobilization of the polymer based structures to improve the forming operation. The lateral trim regions 220 are formed by the trimming process described herein. The lateral trim regions may be produced through the use of dies that are equal to or longer than the length of the forming dies. It can be seen in FIG. 2 that the length of the lateral trim region extends from the tip 120 of the fiber into the main body portion 110 and is extending beyond the terminal edge 290 of the formed tapered region 130. The use of an extended lateral trim region ensures the production of finished formed fibers are cleanly trimmed and any flash, or excess material, present after forming is removed cleanly from the fiber. In an alternative embodiment, it may be desirable to terminate the lateral trim regions at the terminal edge 290 of the formed surface to provide a more uniform appearance. Further, in another embodiment, it may be desirable to terminate the lateral trim region 220 within the formed region thereby leaving a residual lateral extension from each side of the fiber to provide positive features to control the depth of insertion of the fiber tip 120 within the associated needle. As can be seen in the cross-sectional view in FIG. 2A, the perimeter 271 of the reduced cross-section 270 of section 120 of the fiber 110 is formed as two circular segments 250 connected to at least two non-circular segments 240 that have been created through the application of the trimming process described herein. The curved segments 250 share a common center point while the two non-circular segments 240 are substantially parallel to each other, may be symmetrically located at an equidistant offset dimension relative to the central axis 105 of the main body of the suture, and intersect the circular segments at non-tangential locations. The circumference 260 of the filament body 110 is also seen. The trim regions 220 may optionally be produced as multi-faceted elements or polygonal in nature. The trim regions 220 may be described as body flats or facets, although the segments 240 may be curved or have curved and straight segments or consist of plurality of angulated straight segments connected angularly at vertexes. The trim regions 120 and 130 are formed, for example by die cutting, into fiber 110 by the novel processes of the present invention as described herein. Alternatively, if desired, the reduced cross-section 270 may have a perimeter 271 consisting entirely of angulated straight segments to provide a polygonal cross-section, or may have a single curved section connected to at least one angulated straight section. Alternatively, the perimeter 271 may consist of two connected curved sections, such that the resulting cross-section 270 may have a curved configuration such as a circle, ellipse, etc.

In order to produce the desired tapered tip geometry, the main body or fiber 110 of the suture 100 may be processed through the use of either manual or automated processes. An example of a manual process of the present invention is the following. The process initially involves the use of an alignment frame 300 coupled with the use of a forming press, preferably with thermal capability; and, in a secondary operation a formed section of the suture filament 110 is subjected to a stamping process during which the trimming of the excess material produced during the forming operation is removed from the suture filament body 110 and tip 120 through the use of a matched die set. It is within the scope of the present invention to form the novel suture tips of the present invention utilizing an automatic process as well.

Figure 3:
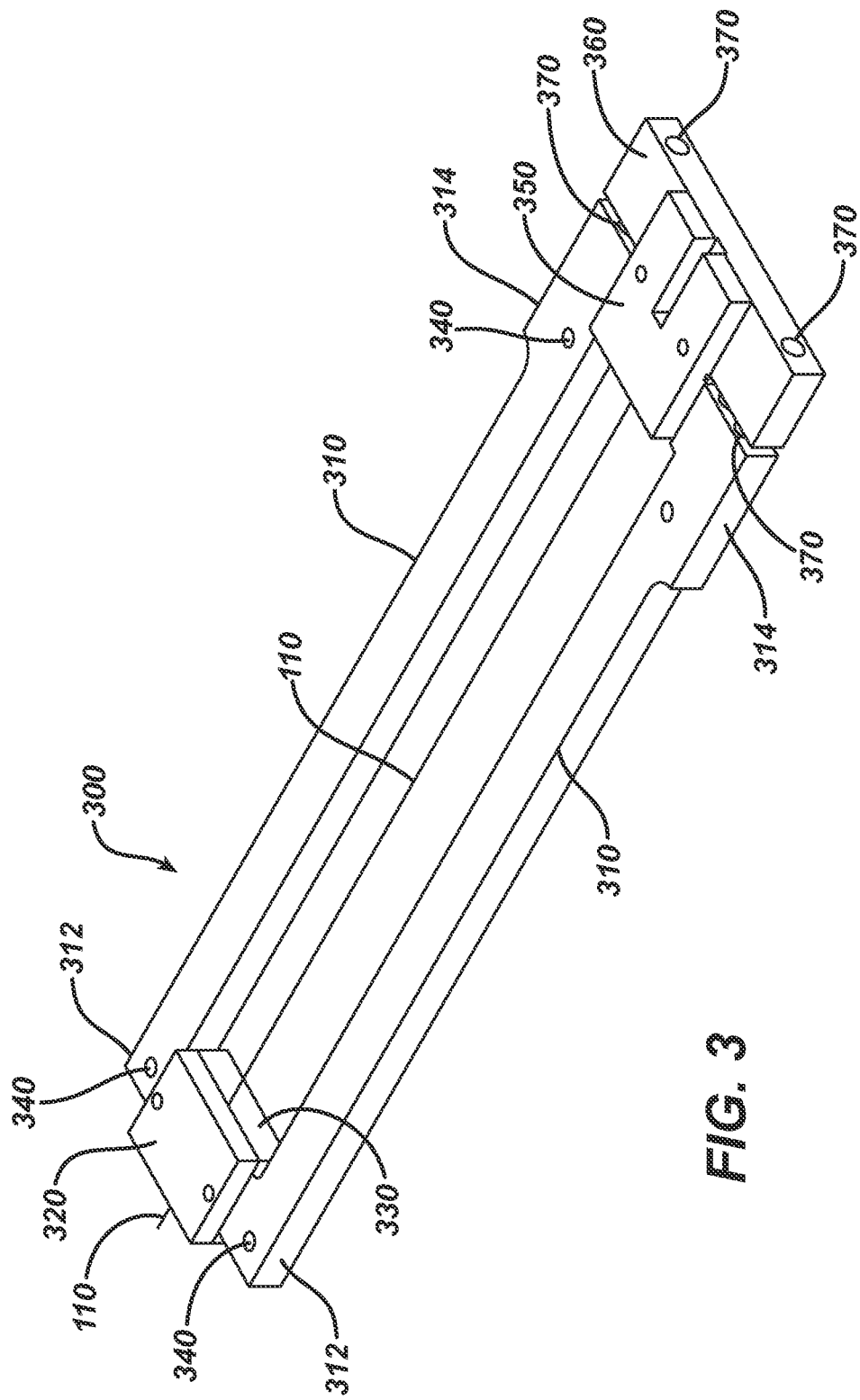
FIG. 3 is a perspective view of an alignment frame useful in the practice of the present invention to form suture tips.

Referring to FIG. 3, the alignment frame 300 is seen to have two spacer rails 310 with a first and second ends 312 and 314, respectively. In each of the ends 312 and 314 of the spacer rails 300, there is at least one alignment pin receiver hole 340. Each first end 312 is coupled to a stationary fiber clamp 320 through the use of the stationary clamp base block 330. Each second end 314 is coupled to a spring loaded fiber clamp 350. The base block 360 of the spring loaded clamp 350 is mounted in sliding engagement on two parallel guide pins 370 extending from the second end 314 of each of the two parallel spacer rails 310. The monofilament suture body 110 to be processed is mounted in the frame 300 through compressive engagement with the clamping elements 320 and 350. Elements 320 and 330, as well as elements 350 and 360 preferably have machined grooves (not shown) for receiving the suture body 110. The grooves are preferably smaller than the suture diameter being formed, but may be the same size or larger.

Figure 4:
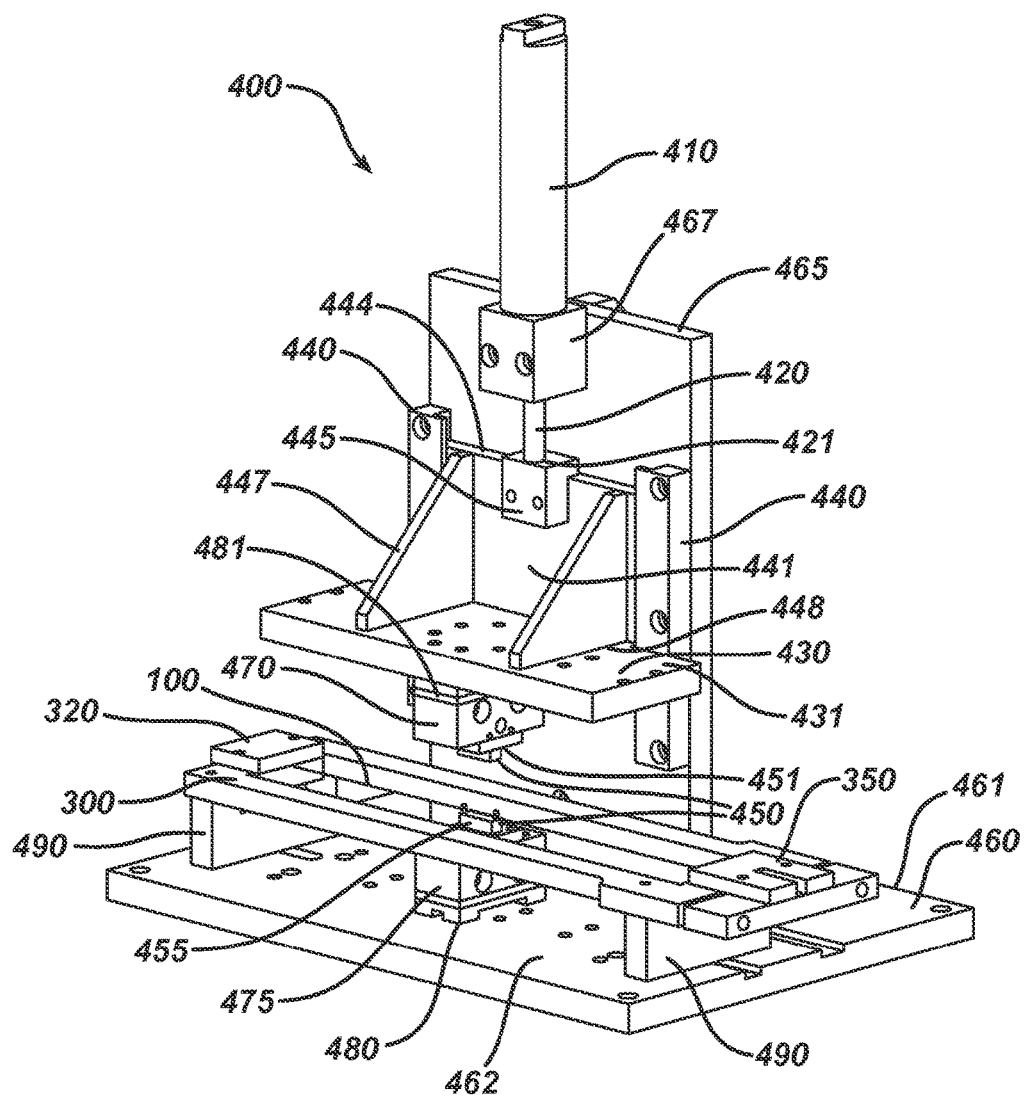
FIG. 4 is a perspective view of a forming press useful with the alignment frame of FIG. 3 to form suture tips.

Referring to FIG. 4, the forming press 400 useful in the practice of the present invention is seen to be comprised of a base platen 460 on which is mounted to side 461 a vertical cylinder support plate 465. Two alignment stand-off blocks 490 are mounted to the top surface 462 of platen 460, and one heater block stand-off plate 480 is also centrally mounted to top surface 462. The alignment frame 300 containing the mounted suture fiber 110 is placed between the operating platens 430 and 460 of the forming press 400 such that the alignment pin receiver holes 340 are engaged with alignment pins 490 located on the top surfaces 491 of the alignment stand-off blocks 490. The cylinder support plate 465 provides support for the air cylinder 410 which is attached to the cylinder support plate 465 through the use of the mounting block 467. Additionally, the free end 421 of the air cylinder shaft 420 is attached to the upper platen slide plate 441 through the use of the shaft mounting block 445. The upper platen slide plate 441 is vertically slidably engaged with the cylinder support plate 465 through the use of two guide rails 440. The upper platen 430 and the two triangularly-shaped buttress plates 447 are fixedly attached to the upper platen slide plate 441. The bottoms 448 of the buttress plates 447 are attached to the top surface 431 of upper platen 430. This configuration enables the upper platen 430 to move vertically relative to the position of the base platen 460 upon activation of the cylinder 410. The forming die 450 is comprised of two mated halves, the upper die 451 and the lower die 455. The upper die 450 is mounted to an upper temperature unit 470, within which are located the conventional heater elements and cooling passages. The lower temperature unit 475 is fixedly attached to the lower die 455, similarly containing conventional heater elements and cooling passages. The temperature units 470 and 475 may be optionally attached to their respective stand-off blocks 480 through the use of intermediary insulator units 481.

Figure 5:
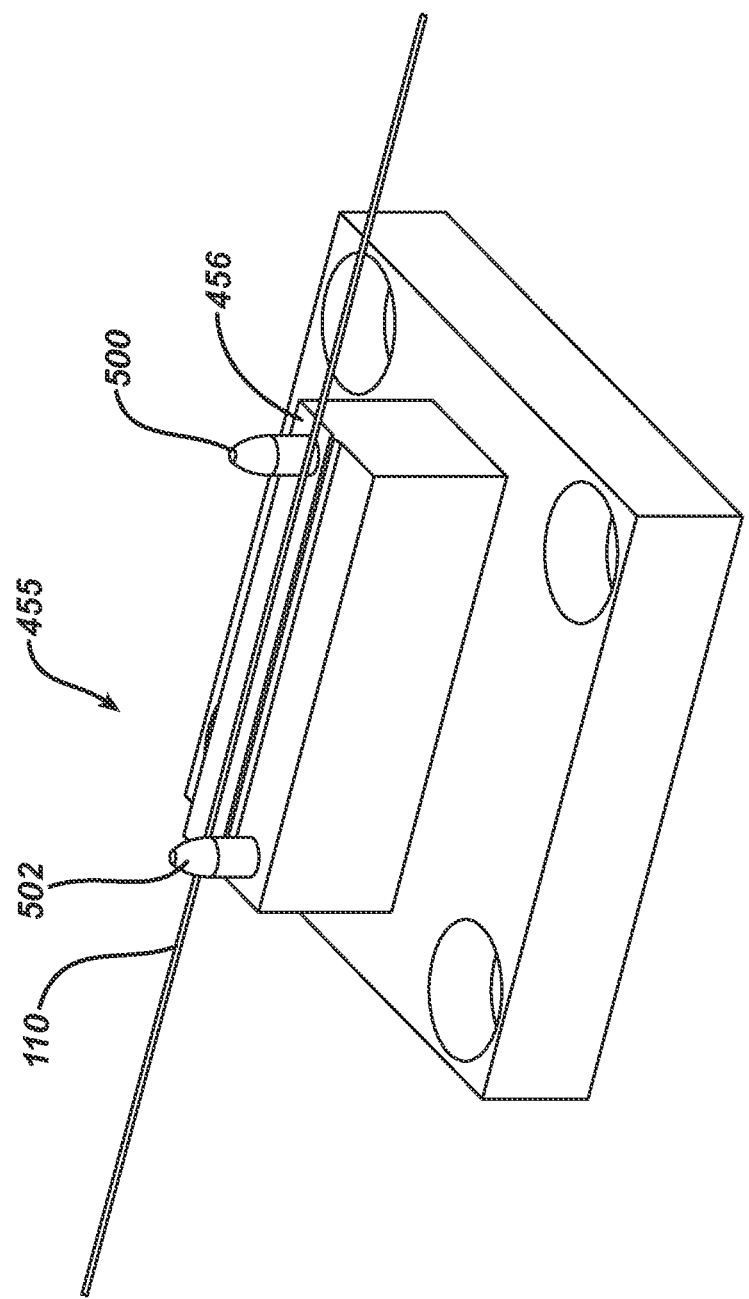
FIG. 5 is a perspective view of the lower forming die showing alignment pins.

Referring to FIG. 5, the lower forming die 455 is seen to preferably have at least two alignment pins 500 extending from the top surface 456 of die 455 that matingly engage with pin receiver holes (not shown) of the upper forming die 450 during the forming operation. The free ends 502 of the pins 500 are preferably tapered, for example bullet-shaped. Suture fiber 110 is seen located horizontally above the die 455 in between the pins 500.

Figure 6:
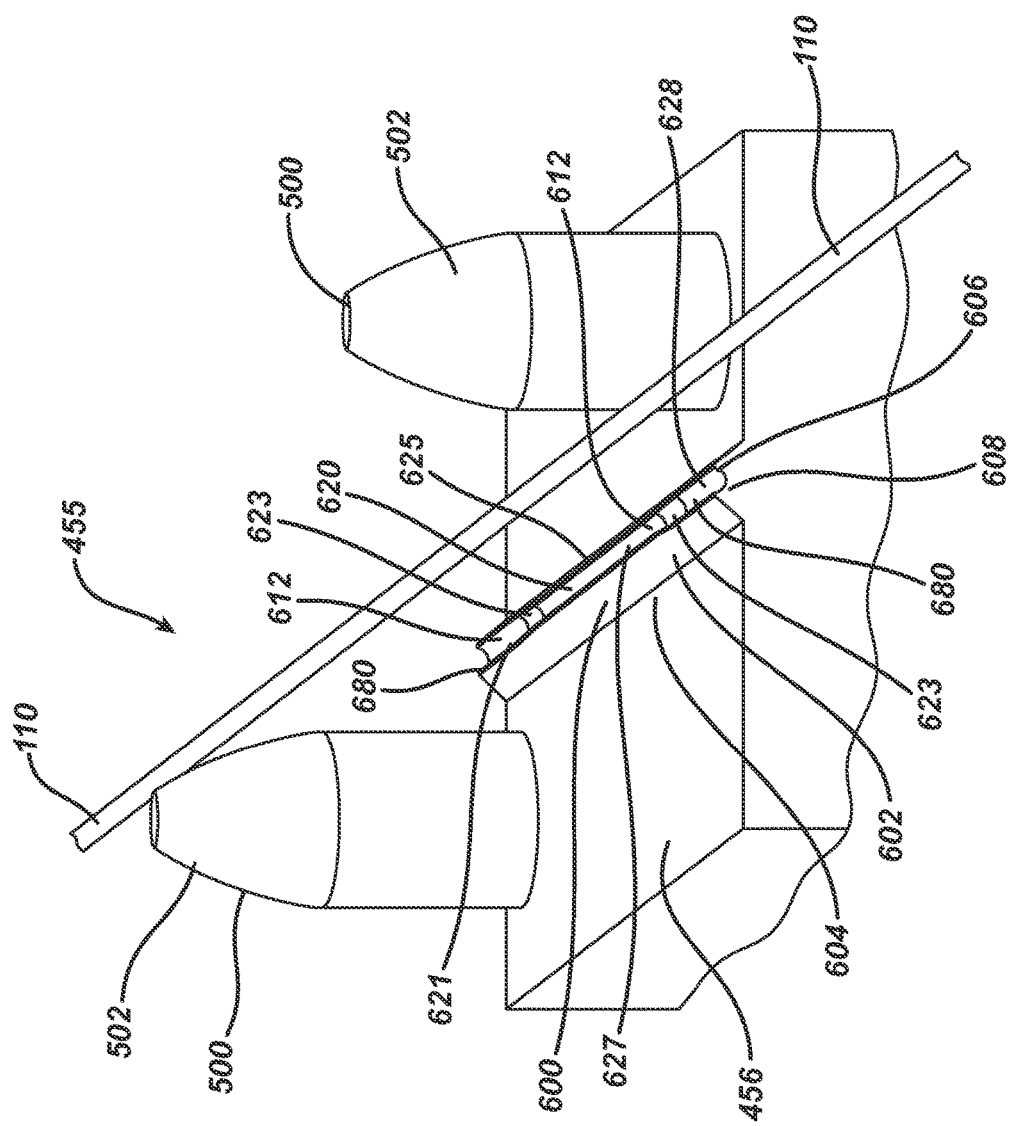
FIG. 6 is a magnified partial perspective view of the lower forming die of FIG. 5.

A magnified partial view of the lower forming die 455 is seen in FIG. 6. The lower forming die 455 is produced with an elongated, centrally located raised portion 600 extending up from surface 456 of forming die 455. Raised portion 600 is seen to have a pair of angulated sides 602 having bottoms 604, top edges 606 and opposed end faces 608. Located within raised portion 600 is the forming channel 620. Channel 620 is seen to be defined by the channel wall 612. The shape of the channel wall 612 will determine the final geometry imparted to the sections 130 and 120 of the suture 100 by the initial forming step. The channel 620 is produced as a continuous depressed axial feature that has a radial shape and open top 628. The channel is also bounded by two edge segments 680 that extend up from the tops edges 606 of raised portion 600. The two edge segments 680 are located at a distance between them that approximates the diameter of the particular suture fiber to be modified. The channel 620 is seen to have first segment 621 corresponding to the full diameter or width of suture filament 110. In abutment to the two edge segments 680 are tapered segments 610 that serve to transition the channel depth/diameter in channel segment 623 from the full suture diameter between edge segments 680 in channel section 621 to the reduced central region diameter in channel segment 625. While the channel 620 is illustrated as a radial depression within the elevated die region, other geometries such as square, triangular or other polygonal shapes may be utilized for the channel 620 in many of these procedures, in the die face. Although not shown, upper die 450 has a similar raised portion 600 with a mirror image forming channel 620.

Figure 7:
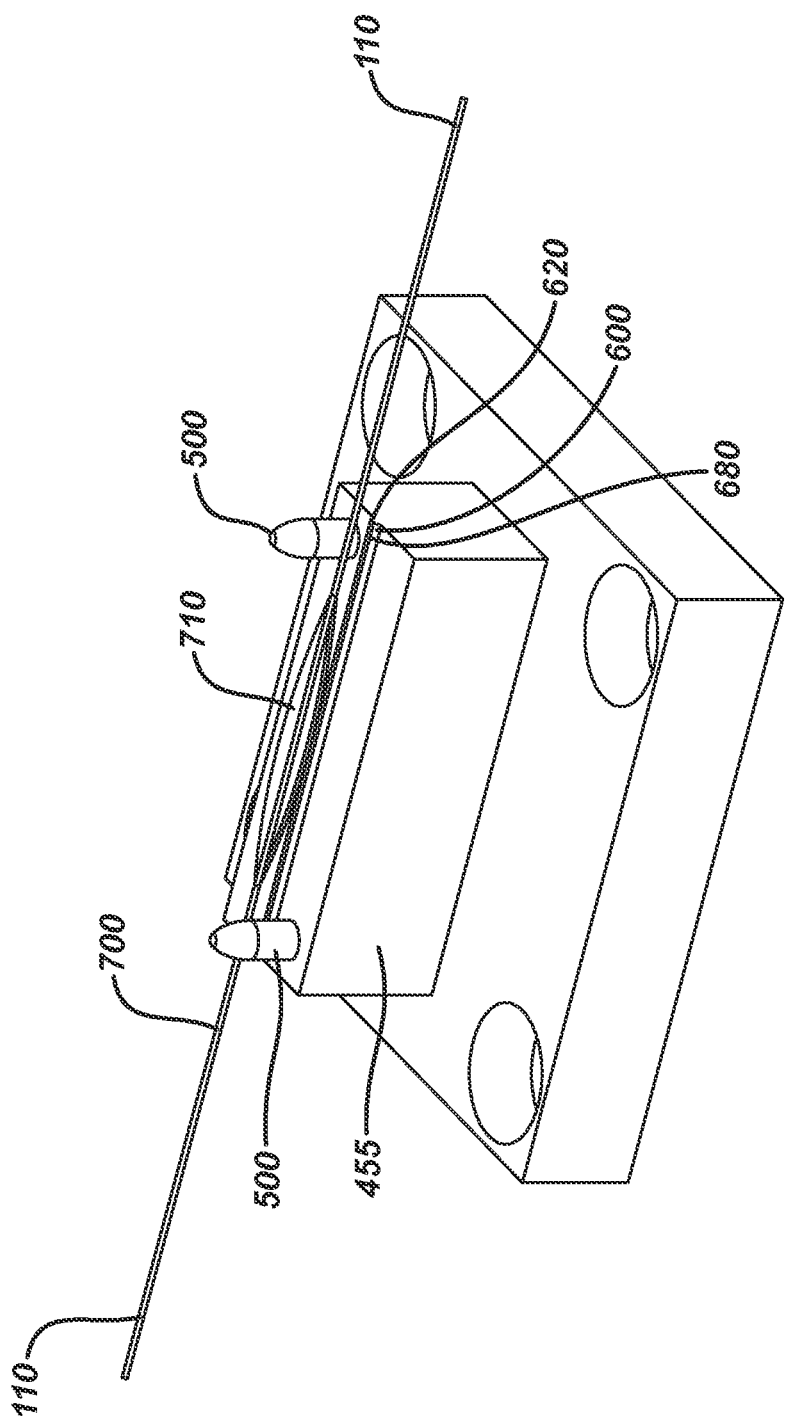
FIG. 7 is a perspective view of the forming die of FIG. 5 showing a monofilament suture with a tip section that has been partially formed.
Figure 8:
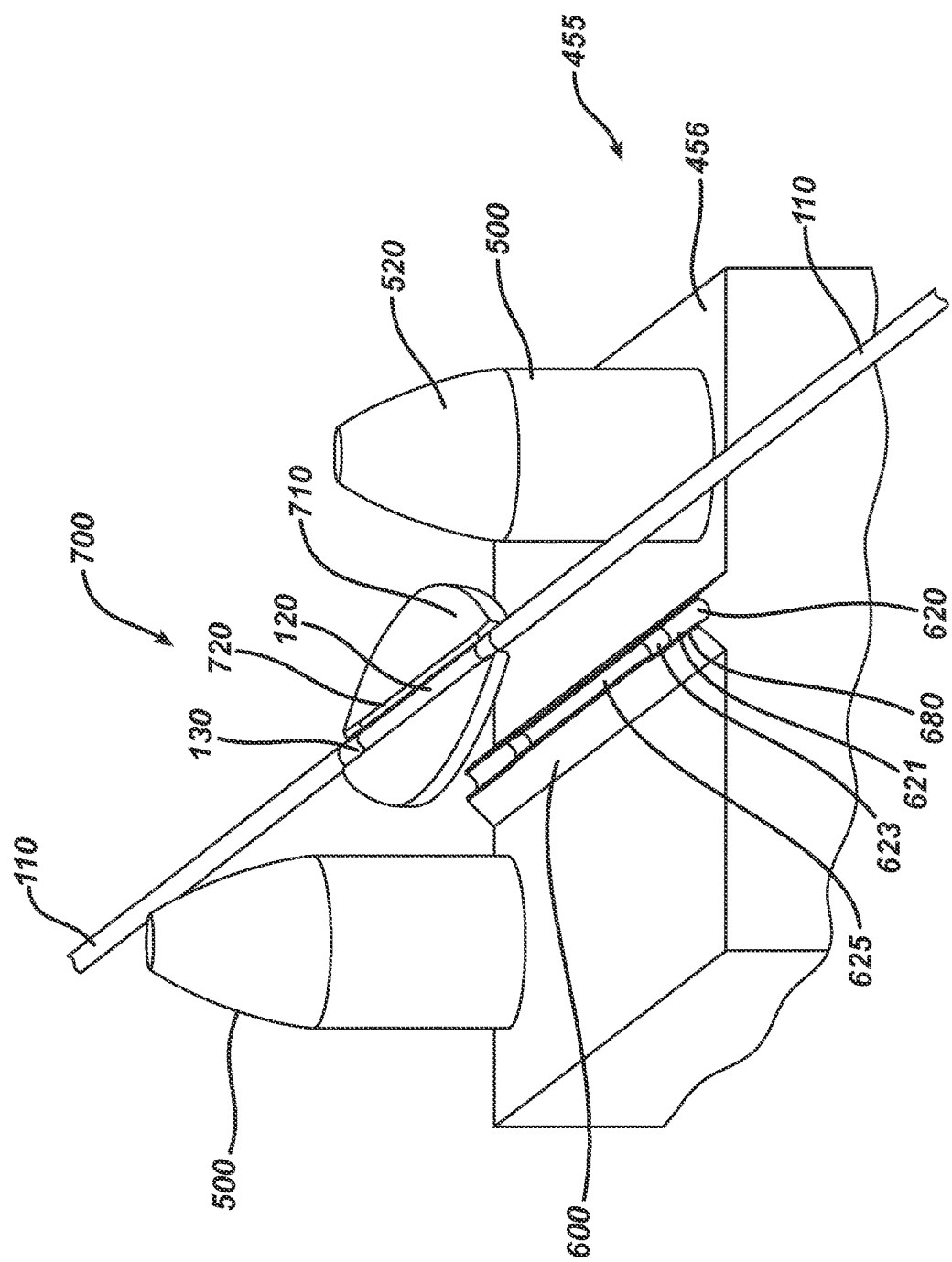
FIG. 8 is a magnified partial perspective view of the forming die and suture of FIG. 7.

Referring to FIGS. 7 and 8, the suture fiber 110 is seen after it has been subjected to the forming operation between dies 450 and 455, and the modified suture is seen to have a tipping blank section 700. The region of the suture blank 700 that has been subjected to forming is expanded laterally to form flattened laterally extending wing regions 710. Wing regions 710 are formed when excess material is forced outwardly from the upper and lower channels 620 as tip sections 120 and tapered section 130 of the suture are formed. The wings are shaped by the flat surfaces 456 and 451 of the dies 450 and 455. Since the forming die 455 is produced with the elevated edge segments 680 along the channel 620 region, the tipping blank section 700 is formed with a "score" line 720 along the edge of the core of the modified fiber. During the forming operation, the fiber 110 may be heated through proximity to the heated forming dies 450 and 455 and is then subjected to pressure until the dies 455 and 450 reach the closed position. This is done by actuating cylinder 410 to move the upper platen 430 to which die 450 is mounted downwardly until die 450 contacts suture fiber 110 and lower die 455. Depending upon the process selected for the specific material, the material may be cooled within the die through the application of cooling medium within the channels of temperature unit. The suture fiber will typically be heated to a sufficient temperature to provide sufficiently effective flow. The temperature will depend upon the composition of the suture, specifically the type of copolymer or polymer. For polymeric devices, typically the temperature will be sufficiently effective to provide the desired material flow and will be between ambient room temperature to a temperature near the melting temperature Tm of the polymer that has been selected. In general, the temperature will be selected on the basis of the material properties of the device, the final tip configuration, etc. However, for certain materials, heating may not be necessary in order to form the tipping blank sections 700 of the suture fibers 110. Optionally, the edge segments 680 may be formed as cutting edges.

Figure 9:
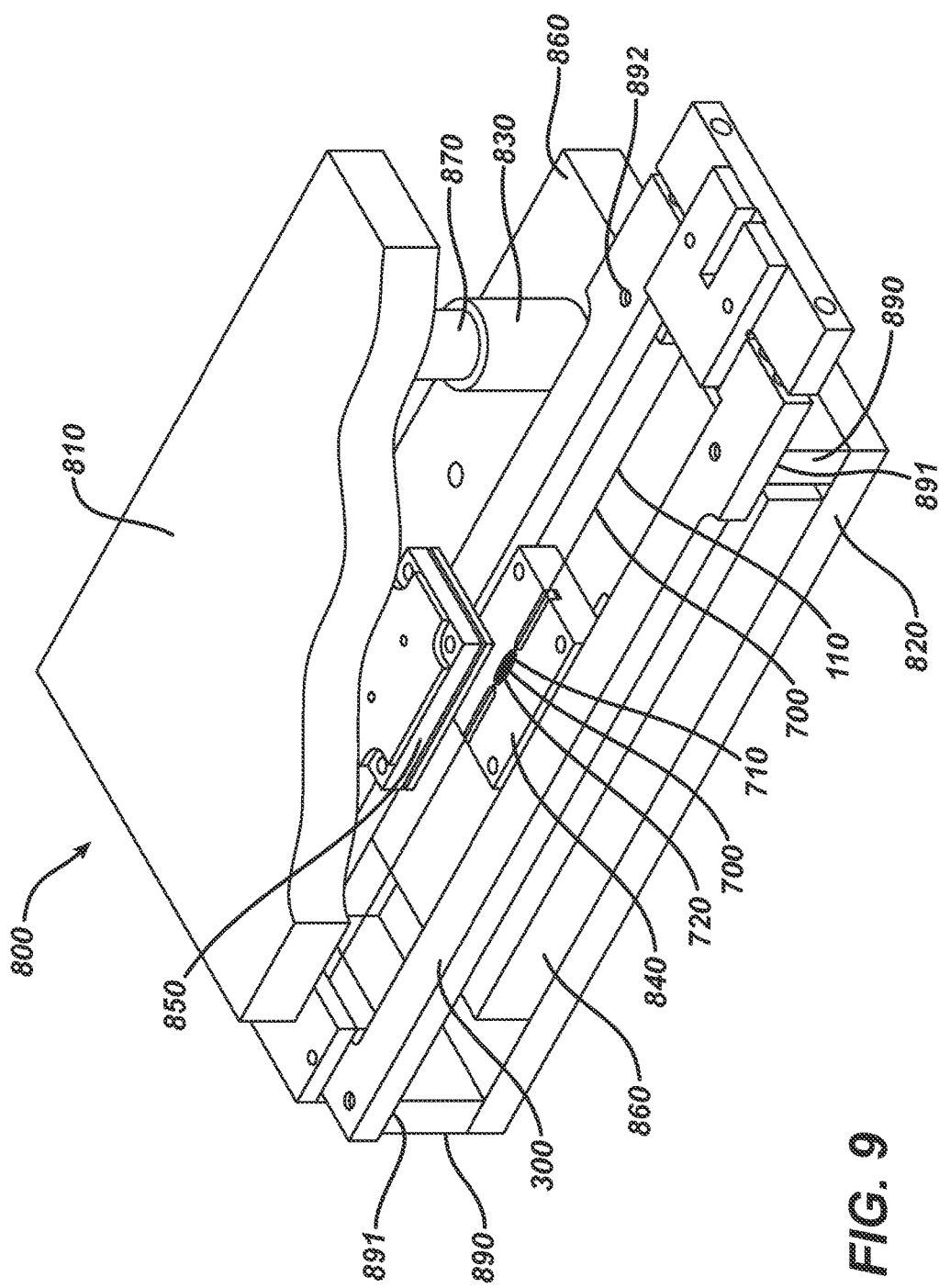
FIG. 9 is a partial cut-away perspective view of a punching die set component of a cutting press useful to cut the suture tips of the present invention after the forming step.

Referring to FIG. 9, a partial cut-away view of a punching die set 800 useful in the practice of the present invention is shown. The punching die set 800 is used after the forming step to trim the suture blank 700. The die set 800 is comprised of an upper die plate 810, and a lower die plate 860, die bushings 830, die posts 870, and die springs that are not shown. The die set 800 is mounted to the punching press base plate 820. Two alignment stand-off blocks 890 are attached to the base plate 820. After forming, the tipping blank 700 remains within the alignment frame 300 and the alignment frame 300 is transferred to the punching die set and is located on the tops 891 of the alignment stand-off blocks 890. The alignment frame 300 is fixed in the proper position within the die set 800 through the presence of the alignment pins 892 located on the tops 891 of the alignment stand-off blocks 890. The punch set is comprised of an upper punch assembly 850 and the lower receiver assembly 840.

Figure 10:
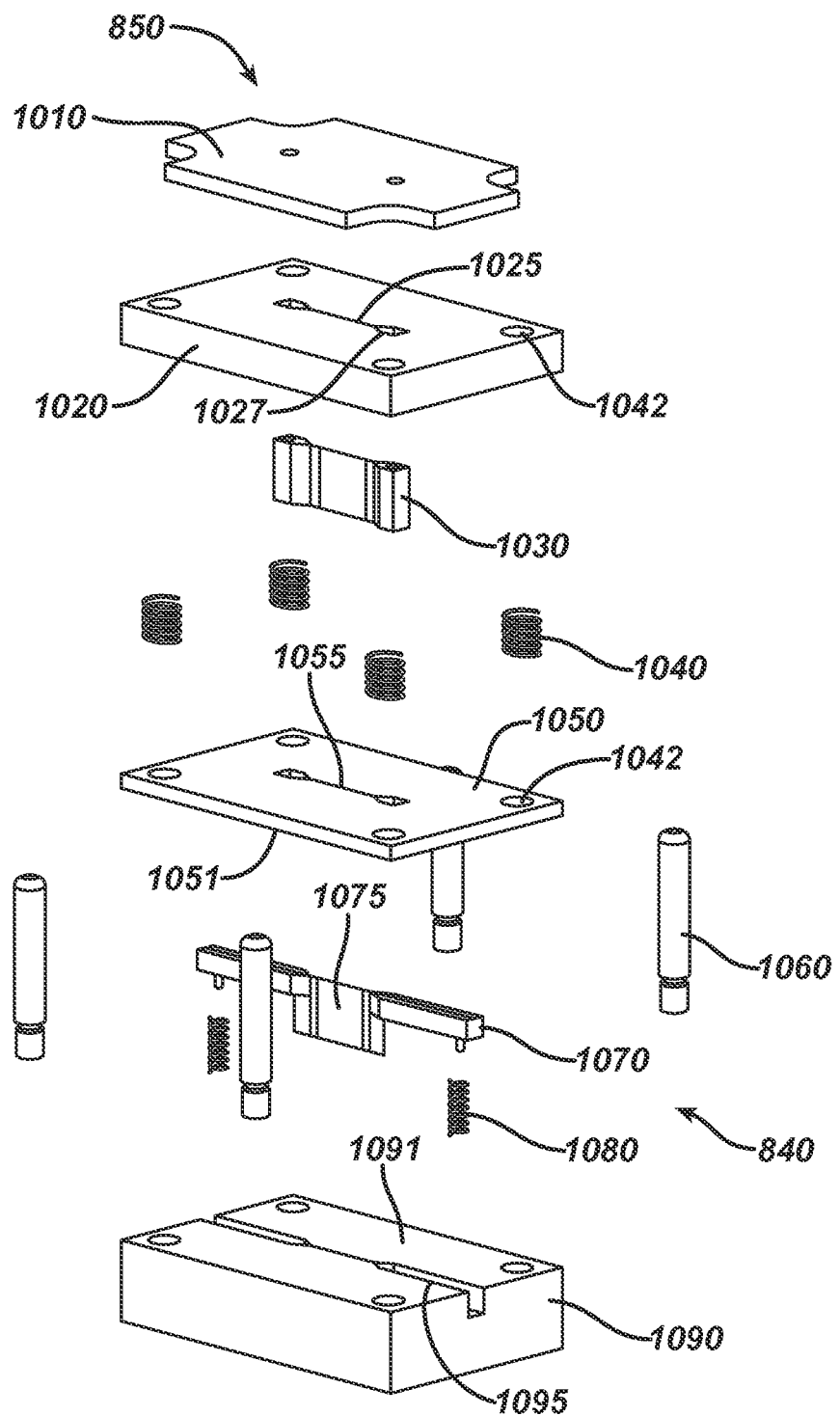
FIG. 10 is an exploded perspective view of the punching die set of FIG. 9.

Referring to FIG. 10, an exploded view illustrating the upper punch 850 and lower receiver 840 assemblies is seen.

The punch assembly 850 is comprised of three main subassemblies. The punch 1030 and punch guide plate 1020 are assembled in abutment with the punch base plate 1010. The punch 1030 is fitted into a mating slot 1027 within the punch guide plate 1025. Additionally, four stripper springs 1040 are utilized in the assembly. The stripper springs 1040 are placed in between the punch guide plate 1020 and the lower stripper plate 1050 and may be held in place in pockets or bore holes 1042 that have been machined in each abutting plate. Additionally, the punch guide plate 1020 and stripper plate 1050 are held together through the use of shoulder bolts (not shown) that pass through the stripper springs 1040. The punch 1030, punch guide plate 1020 and the base plate 1010 are secured together to prevent relative motion of the components. The stripper plate 1050 is capable of motion relative to the other components that have been secured together. Also seen in the stripper plate 1050 is the slot 1055 that generally matches or conforms to the profile of punch 1030. The receiver assembly 840 is comprised of the receiver base plate 1090 with a receiver slot 1095 machined into the plate 1090, ejector springs 1080, the ejector bar 1070 and the die guide bolts 1060. The ejector springs 1080 are placed within the receiver slot 1095 and the ejector bar 1070 is pressed down on top of the ejector springs 1080. The ejector bar 1070 is then fixed to the receiver base plate 1090 in slidable engagement. The ejector bar 1070 is seen to have narrow region 1075 that is matched to the shape and size of the formed suture region.

Figure 11:
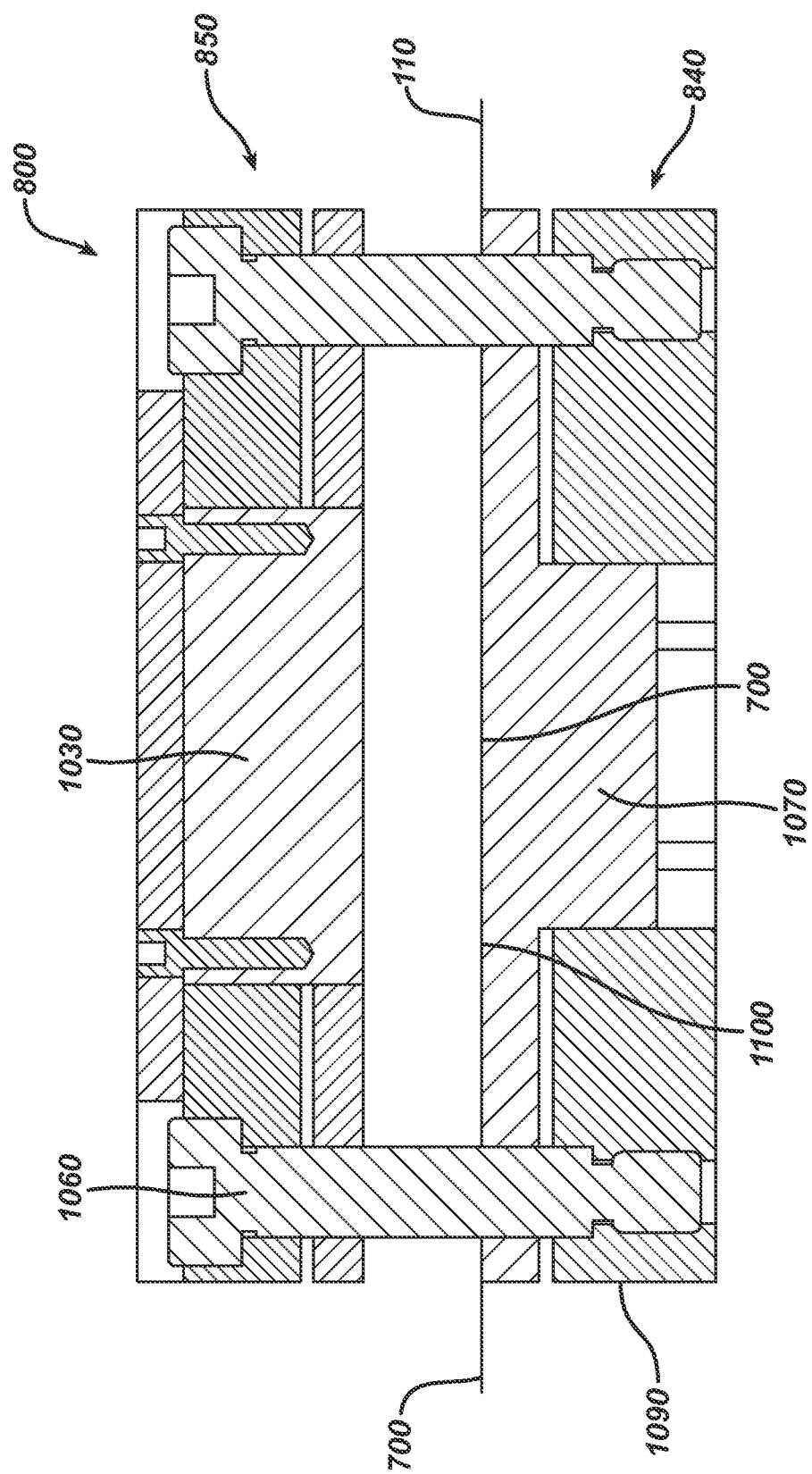
FIG. 11 is a cross-sectional view of the assembled punching die set of FIG. 10 in the open pre-punching position.

FIG. 11 is an illustration of the cross-sectional views of the assembled punching die set 800 in the open pre-punching position. The die guide bolts 1060 serve to secure the punch assembly 850 to the lower receiver assembly 840. The return springs 1040 and ejector springs 1080 are not included in the view. The tipping blank 700 is shown in position over the lower receiver die face 1091/ejector bar 1070 unit in preparation for the trimming operation. The tipping blank 700 is located in close proximity to the plane of the upper surface of the receiver base plate 1090/upper surface of the ejector bar 1070.

Figure 12:
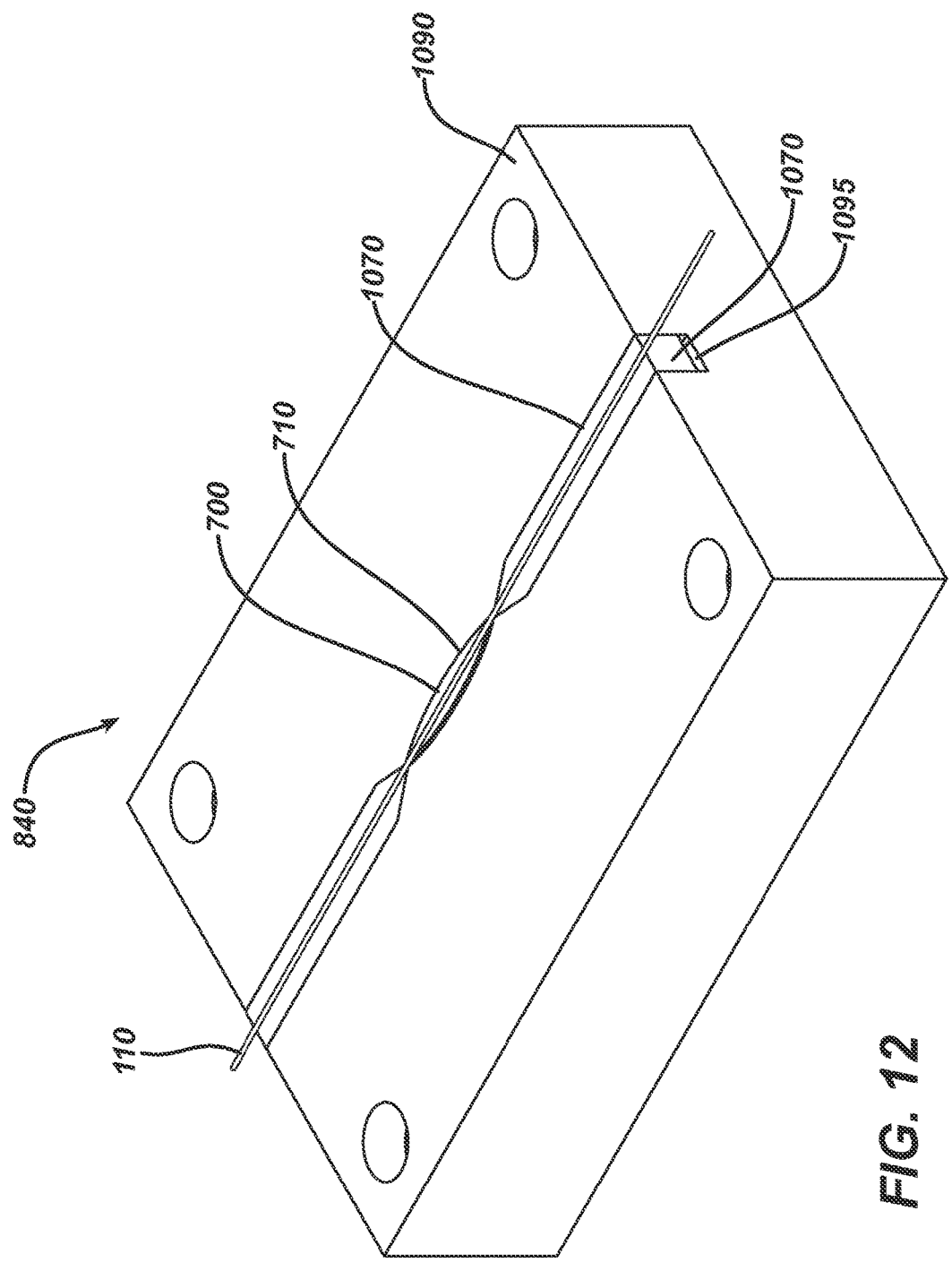
FIG. 12 is a perspective view of the pre-formed suture in the lower punching die.

Referring to FIG. 12, the tipping blank 700 is illustrated, in a close up view, above the ejector bar 1070 in the receiver assembly 840. The punch assembly 850 is not shown. The tipping blank 700 section having the expanded lateral width portion 710 is positioned with the flat planar surface of the modified fiber parallel to the plane of the die surface.

Figure 13:
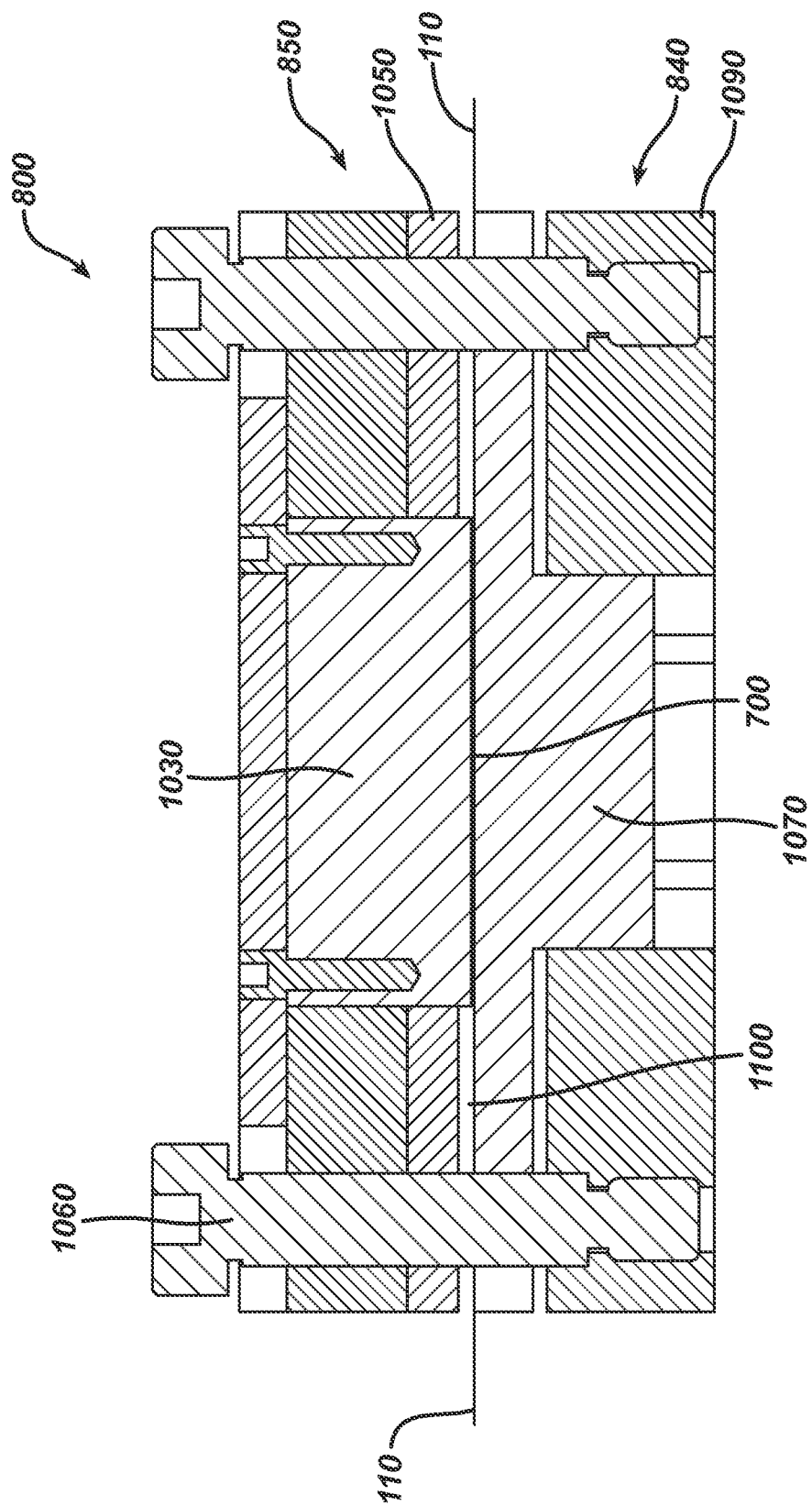
FIG. 13 is a cross-sectional view of the assembled punching die set during the maximum downward stroke of the punching press.

Referring to FIG. 13, a cross-sectional view of the assembled punching die set 800 during the maximum downward stroke of the punching press is seen. During the downward stroke, the punch base plate 820/punch guide plate 1020/base plate 1090 assembly are compressed against the stripper plate 1050 once the stripper plate 1050 bottoms out against the lower receiver assembly 1090. The punch 1030 is slidably engaged with the stripper plate 1050 and as the die assemblies 850 are compressed together, the stripper plate 1050 strikes the surface of the receiver die 1090, the return springs 1040 are compressed against the punch base plate 1020/punch guide plate 1020/base plate 1090 assembly and the punch 1030 passes through the lower face 1051 of the stripper plate 1050 and enters into the lower receiver 1090. As the punch 1030 enters the lower receiver 1090, the tipping blank 700/110 is pressed against the ejector bar 1070 which presses against the ejector springs 1080 located under the ejector bar 1070 and the punch 1030 travels into the lower receiver 1090. As the tipping blank 700 and ejector bar 1070 travel further into the lower receiver 1090, the expanded region 710 of the tipping blank 700 strikes the edge 1070 of the lower receiver 1095 and is sheared off from the tipping blank 700/110 to form the finished trimmed suture 100. The trimmed blank section 700 is divided into two tipped sutures 100. They are cut manually after trimming but a shear section can be built into the trim die 800 for a continuous production version.

Figure 14:
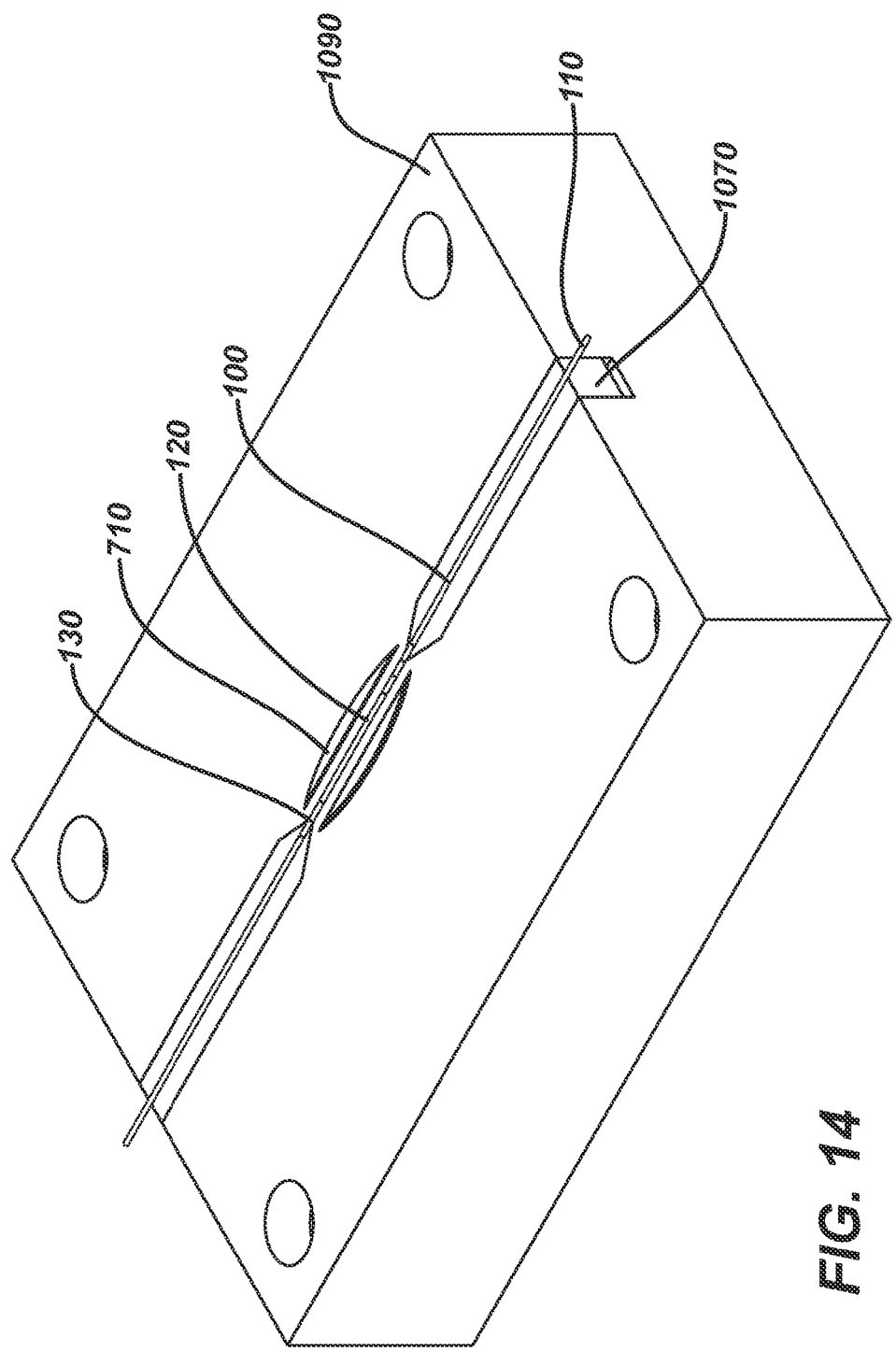
FIG. 14 is a perspective view of the finished trimmed and tipped suture in position above the ejector bar in the receiver assembly; the lateral trimmed waste is seen proximate the formed tip.

FIG. 14 is an illustration of the finished trimmed suture 100 in position above the ejector bar 1070 in the receiver assembly. For illustrative purposes, the trimmed lateral waste sections 710 have not been removed from the face of the receiver assembly.

Although the forming and cutting operations have been described as utilizing a separate forming press and a separate punch press, the forming and cutting operations may be performed with a single press apparatus combining the forming components and the punch or cutting components. In addition, when the edge segments 680 are formed as cutting edges, the use of a separate cutting die may not be required to trim the suture tip and/or transition section.

It should be noted that although the apparatus of the present invention as described and illustrated is symmetrical, the apparatus of the present invention may also be designed and constructed to be asymmetrical. In such an asymmetric configuration only a single formed and shaped tip section 120 would be produced on an end of the suture filament 110 to produce the suture 100 having novel tip sections 120. During the asymmetric forming process, the filament section 110 adjacent to tip 120 would be cut to have a plain cut end with diameter 112.

Figure 15:
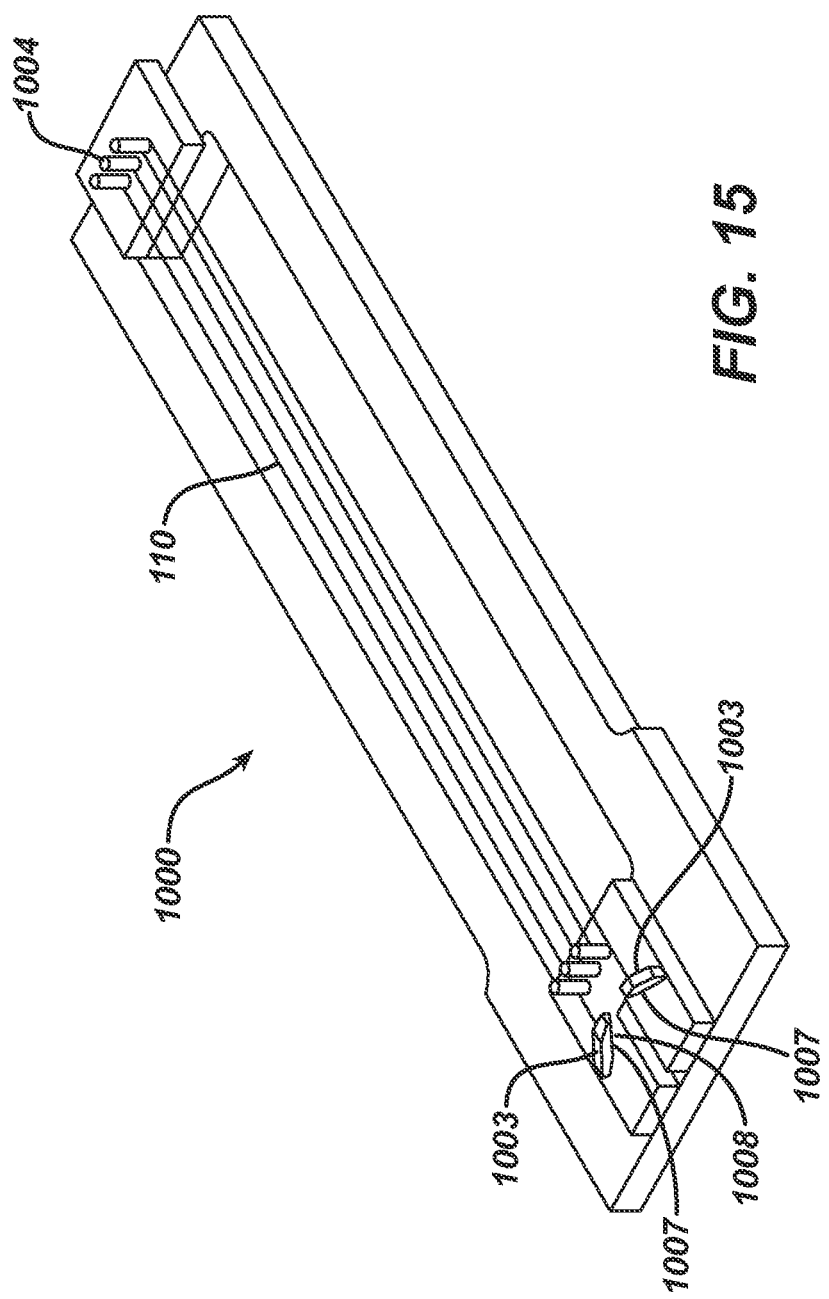
FIG. 15 is a perspective view of an alignment frame useful in the method and apparatus of the present invention for the production of multiple formed fibers.

An alternative embodiment for the production of multiple formed fibers on a manual process is also disclosed. Referring to FIG. 15, the alignment frame 1000 is produced with a series of pins 1004 that serve as a winding fixture for a continuous strand of suture. As can be seen, the suture 110 is wrapped in a serpentine pattern about six pins 1004. Three pins 1004 are located at each end of the winding frame 1000. It can be seen that through the use of the winding method, the fiber is properly oriented to the axis of the frame 1000 through the proximity to the edges of the two opposed winding pins 1004. This alignment methodology eliminates that need for machined suture receiving grooves within a clamping surface. An additional feature of the winding style alignment frame 1000 is the incorporation of the clamping wedge elements 1003. The wedge clamps 1003 are stationary and are produced with a converging slit or "V" groove 1008. The free ends 1007 of the fiber 110 are forcibly pulled into the slits 1008 during the winding operation. Subsequent at rest suture motion is prevented due to the fiber wedging against the edge of the slit 1008. This method of suture securement provides a rapid means for the loading of the alignment frame 1000.

It can be seen that when utilizing the winding style alignment frame that the subsequent forming and trimming operations require modification. Both the forming die and the trimming die are produced with multiple parallel forming and trimming features that will form and trim each length of fiber within the alignment frame.

While the process of the present invention has been illustrated and described as a manual process whereby the fiber is held in a fixed position within a clamping frame, it is anticipated that the process would be automated utilizing a spool feed type continuous process.

In the spool feed process, the suture fiber to be tipped is fed from a payout spool into the tipping forming unit. The leading end of the fiber is positioned within an indexing head. The indexing head draws the fiber into a heating/forming station. The heating forming station may be configured with a set of forming dies similar to the ones previously disclosed. The dies may be mounted for vertical travel and may optionally be heated. Alternatively, the die may be run only in a cooled configuration. The heating of the fiber may be achieved through the use of a heating source that is located at the same axial position as the forming die station along the length of the suture. The heating source is positioned in a plane that is rotated 90 degrees relative to the plane of the forming station, for example, if the forming station traverses vertically, then the heating station is mounted in the horizontal position to provide heating of the fiber while the fiber is positioned within the forming station. Heating sources include but are not limited to conventional infrared heaters, heated convection mediums such as air streams, or other conductive sources such as heated dies, and the like and equivalents thereof.

The operation of the forming station for some polymeric materials involves the application of heat to the fiber and then the subsequent application of the forming die contact and pressure. The forming die, which may be operating at a lower temperature than the heating source, imparts the reshaping of the fiber while the die contact serves to cool the fiber during the forming step. Alternatively, for materials that have a $T_g$ that is lower than room temperature, the heating of the material may not be necessitated and the forming operation may be conducted at ambient room temperature.

Upon completion of the forming step, the formed fiber is advanced to the trimming station whereby the punch and receiver dies are engaged to trim the excess material from the formed fiber. The trimming die may be configured to cut the fiber near and within the reduced cross sectional region of the tipping blank to provide a finished length of fiber from the previously advanced and tipped fiber.

The fiber is not exposed to elevated tension during the heating/forming operations. The fiber feeding mechanism only advances the indexed amount of fiber through both the payout and take-up mechanism maintaining the same relative motion of the fiber.

The use of the trim form process of the present invention ensures that the tipped sutures are always dimensionally consistent providing an improved degree of precision not capable with bulk processing such as extrusion or roll forming. This dimensional consistency enables repeatable attachment strengths when surgical needles are swaged onto the trimmed tips. Additionally, other features, such as indents, corrugations, opposing partial spirals or raised features, may be formed on the fiber tip geometry. The incorporation of these features may improve the needle attachment strength.

Additionally, fiber fibrillation due to over drawing of the fibers is avoided and the rigidity of the tipped fiber is not increased relative to the main body of the suture.

Although this invention has been shown and described with respect to detailed embodiments thereof, it will be understood by those skilled in the art that various changes in form and detail thereof may be made without departing from the spirit and scope of the claimed invention.

We claim:

1. A method of tipping a monofilament surgical suture, comprising the steps of:
   providing a length of monofilament surgical suture having a first end, a second end, and a body having a maximum cross-sectional dimension;
   forming a section of the suture body into a tipping blank between the first and second ends, the tipping blank comprising two transition sections connected by a tip section; and,
   cutting the tipping blank such that at least the tip section has a trimmed region, and dividing the tip section to provide two separate tipped sutures, each tipped suture having a transition section and a divided tip section having a trimmed region, the divided tip section of each suture having a maximum cross-sectional dimension, and the divided tip section of each suture having a configuration comprising opposed arcuate sections joined by flat or linear sections, wherein the maximum cross-sectional dimension of the divided tip section of each suture is less than the maximum cross-sectional dimension of the body of the suture.

2. The method of claim 1, wherein the formed section of suture is formed in a forming apparatus.

3. The method of claim 1 wherein at least part of the formed section is cut with a cutting die.

4. The method of claim 1, wherein only the tip section of the tipping blank is cut.

5. The method of claim 1, wherein at least part of the transition sections and the tip section of the tipping blank are cut.

6. The method of claim 1, comprising the additional step of heating the suture.

7. The method of claim 1, wherein each transition section of the tipping blank is tapered.

8. The method of claim 1, wherein the configuration of each divided tip section comprises at least one curved section and at least one straight section.

9. The method of claim 1, wherein the configuration of each divided tip section comprises at least two curved sections.

10. The method of claim 1, wherein the suture comprises a biocompatible polymer.

11. The method of claim 10, wherein the polymer is an absorbable polymer.

12. The method of claim 10, wherein the polymer is a non-absorbable polymer.

13. The method of claim 11, wherein the absorbable polymer comprises a polymer selected from the group consisting of lactide, glycolide, polylactic acid, polyglycolic acid, poly(p-dioxanone), polycaprolactone, and copolymers and blends thereof.

14. The method of claim 12, wherein the non-absorbable polymer comprises a polymer selected from the group consisting of nylon, polyesters, and polyolefins.

15. The method of claim 1, wherein the trim region extends into the suture body.

* * * * *